United States Patent [19]

Zoeller

[11] Patent Number: 4,783,548

[45] Date of Patent: Nov. 8, 1988

[54] PROCESSES FOR PREPARING 3,4-DIHYDRO 2-NAPHTHANOIC ACID AND 2-NAPHTHANOIC ACID AND ESTERS THEREOF

[75] Inventor: Joseph R. Zoeller, Kingsport, Tenn.

[73] Assignee: Eastman Kodak Company, Rochester, N.Y.

[21] Appl. No.: 97,021

[22] Filed: Sep. 16, 1987

[51] Int. Cl.[4] .................. C07C 149/40; C07C 67/30
[52] U.S. Cl. .......................... 560/10; 560/8; 560/51; 560/56; 560/80; 560/100; 562/405; 562/427; 562/462; 562/466; 562/467; 562/488; 562/490
[58] Field of Search .......... 560/8, 10, 100, 51, 560/56; 562/490, 405, 427, 462, 466, 467

[56] References Cited

PUBLICATIONS

Hurd, "The Pyrolysis of Carbon Compounds," ACS Monograph, Series, No. 50, pp. 532–533 (1929).
House, "Modern Synthetic Reactions," 2nd Ed., pp. 34–44 (1972).
Kuhn, Chem. Ber., 64, 2347–52 (1931).
Radcliffe, J. Org. Chem., 42, pp. 297–300 (1977).
Volkovitch, J. Am. Chem. Soc., 97, pp. 901–902 (1975).
Gasparrini et al, Tetrahedron, 40:1491 (1984).
Jones, Org. Reactions, 15:204 (1967).
Dinulescu et al, Tetrahedron, Supplement 1:37:55 (1981).
Vebrel et al, Bull. Chim. Soc. Fr., Part II:116 (1982).
Ito et al, J. Org. Chem., 39:2769 (1974).
Myrboh et al, J. Org. Chem., 48:5327 (1983).
Kresze et al, Tetrahedron, 34:697 (1978).
Hansch, Chem Rev., 53:353 (1953).
Pines et al, J. Org. Chem., 30:3530 (1965).
Kolomnikov et al, Russ. Chem. Rev., 43:399 (1974).

Primary Examiner—Michael L. Shippen
Attorney, Agent, or Firm—Charles R. Martin; William P. Heath, Jr.

[57] ABSTRACT

A process for preparing a 3,4-dihydro 2-naphthanoic acid or an ester thereof comprises heating an alpha-vinyl cinnamic acid or a ($C_1$–$C_{12}$)alkyl, ($C_6$–$C_{12}$)aryl, ($C_6$–$C_{12}$)aralkyl or ($C_6$–$C_{12}$)alkylaryl ester thereof at a temperature effective to cyclize said acid or ester thereof and obtain the corresponding 3,4-dihydro 2-naphthanoic acid or ester thereof. The alpha-vinyl cinnamic acid or ester thereof may be obtained by contacting crotonic anhydride and a benzaldehyde substituted with halo or ($C_1$–$C_{12}$)alkyl, acyl, acyloxy, carboxy, carbalkoxy, alkylthiol or alkoxy.

A process for preparing 2-naphthanoic acid or an ester thereof comprises the above steps to prepare a 3,4-dihydro-2-naphthanoic acid, and dehydrogenating said 3,4-dihydro 2-naphthanoic acid or ester thereof to obtain the 2-naphthanoic acid.

8 Claims, No Drawings

PROCESSES FOR PREPARING 3,4-DIHYDRO 2-NAPHTHANOIC ACID AND 2-NAPHTHANOIC ACID AND ESTERS THEREOF

BACKGROUND OF THE INVENTION

1. Field of the Invention

The present invention relates to a novel process for preparing 3,4-dihydro 2-naphthanoic acids or esters thereof by heating an alpha-vinyl cinnamic acid or ester thereof to attain cyclization. The invention also relates to a process for preparing 2-naphthanoic acids or esters thereof by first obtaining a 3,4-dihydro 2-naphthanoic acid or an ester thereof as indicated above, and then dehydrogenating this compound to obtain the corresponding 2-naphthanoic acid or ester thereof.

2. Description of the Background

Substituted 2-naphthanoic acids and esters thereof are useful as polymer intermediates in the chemical industry. However, the methodology for making these compounds is very sparse. The major problem posed by the synthesis of these compounds is that for the 2-naphthanoic acid derivatives to be useful as polymer intermediates, a second functional group besides the carboxyl group must be present. Moreover, such functional group must be present at a specific location on the molecule. Thus, a single, specific isomer of a disubstituted 2-naphthanoic acid or ester thereof must be produced out of a potential 14 distinguishable isomeric naphthanoic acids. The development of such a process is of great significance to the industry. Dihydronaphthanoic acids or esters particularly the 3,4-isomer, are particularly valueable substituted 2-naphthanoic acids.

A number of methods have been known to produce dihydronaphthalenes, including one with a pyrolytic approach similar to the present invention (Volkovitch, P. B., Conger, J. L., Castiello, F. A., Brodie, T. D. and Webber, W. P., J. Amer. Chem. Soc. 97: 901 (1975); Radcliffe, M. M., and Webber, W. P., J. Org. Chem. 42: 297 (1977); Rosen, B. I., and Webber, W. P., Tet. Lett. 51 (1977); Rosen, B. I., and Webber, W. P., J. Org. Chem. 42: 47 (1977)). However, none of the prior art methods are applicable to the synthesis of 3,4-dihydro 2-naphthanoic acid derivatives with a predictable substitution pattern.

Specific 3,4-dihydro-2-naphthanoic acids have been synthesized by the prior art (Myrboh, B., Ila, H., Junjappa, H., J. Org. Chem. 48: 5327 (1983); Dinulescu, I. G., Georgescu, E. G., Stanescu, L., and Avram, M., Tet. Suppl. 1, 37: 55 (1981); Vebrel, J., and Carrie, R., Bull. Chim. Soc. Fr., Part II: 116 (1982); Ito, Y., Yonezawa, K., and Saegusa, T., J. Org. Chem. 39: 2769 (1974)). However, none of these specifically tailored methods are applicable to the general class of naphthanoic acid derivatives synthesized by the process of this invention.

Accordingly, there is still a need for a general process for the synthesis of dihydronaphthanoic acid and naphthanoic acid derivatives having a predictable substitution pattern.

SUMMARY OF THE INVENTION

This invention relates to a process for preparing a 3,4-dihydro 2-naphthanoic acid or an ester thereof which comprises heating an alpha-vinyl cinnamic acid or a $(C_1-C_{12})$alkyl, $(C_6-C_{12})$aryl, $(C_6-C_{12})$alkylaryl or $(C_6-C_{12})$aralkyl ester thereof at a temperature effective to cyclize said acid or ester thereof and obtain the corresponding 3,4-dihydro 2-naphthanoic acid or ester thereof.

This invention also relates to a process for preparing a 2-naphthanoic acid or an ester thereof which comprises heating an alpha-vinyl cinnamic acid or a $(C_1-C_{12})$alkyl, $(C_6-C_{12})$aryl, $(C_6-C_{12})$alkylaryl or $(C_6-C_{12})$aralkyl ester thereof at a temperature effective to cyclize said acid or ester thereof and obtain a 3,4-dihydro 2-naphthanoic acid or ester thereof; and dehydrogenating the 3,4-dihydro 2-naphthanoic acid or ester thereof to obtain the corresponding 2-naphthanoic acid or ester thereof.

A more complete appreciation of the invention and many of the attendant advantages thereof will be readily perceived as the same becomes better understood by reference to the following detailed description of the preferred embodiments thereof.

DESCRIPTION OF THE PREFERRED EMBODIMENTS

The process for preparing a 3,4-dihydro 2-naphthanoic acid or an ester thereof of the invention relies on a thermal ring closure of an alpha-vinyl cinnamic acid or ester thereof. The cyclization may be performed either in the liquid or vapor phases, with the latter being generally preferred since it can be conducted even in the absence of solvent and produces generally higher yields of product. Moreover, when the thermal cyclization is conducted in the vapor phase, no purification of the product is required. Furthermore, the 3,4-dihydro 2-naphthanoic acid product or the ester thereof obtained from the vapor phase reaction are in a very pure state, generally containing solely the corresponding naphthalene as the only detectable impurity. The amount of naphthalene impurity is generally less than about 1 wt % to 3 wt % of the product.

When the cyclization is conducted in the vapor phase, it is done at a temperature of about 200° C. to 800° C., and more preferably about 350° C. to 550° C. and a pressure of about 0.1 mmHg to 5 atm, and more preferably about 10 mmHg to 1500 mmHg. However, much higher temperatures can also be used without difficulty, such as temperatures in excess of about 800° C. These temperatures are easily attainable in an industrial environment. More commonly, the vapor phase cyclization reaction is conducted at ambient pressure using an inert gas purge to promote the transport of materials across a pyrolysis chamber. However, any feasible pressure below atmospheric pressure may suitably be employed and actually serves to promote the vaporization of the starting acids or esters. By means of example, a pressure of about 10 mmHg can be attained in an industrial environment. Higher pressures than those described above may also be employed, particularly in the case where the starting acids or esters are volatile. However, due to the need to vaporize the starting material the pressure is practically limited to about several atmospheres.

When the thermal ring closure is conducted in a liquid phase, an inert solvent is utilized. Any high boiling solvent may be utilized as the inert solvent at atmospheric pressure. Lower boiling point solvents can be used if the reaction is conducted under pressure, i.e., in an autoclave, thereby attaining the desired temperature while preserving the solvent in the liquid phase. When the process is conducted in the liquid phase it is typically done so at a temperature of about 150° C. to 500° C., and more preferably at about 180° C. to 400° C.

The inert solvent must have a boiling point equal to or greater than the reaction temperature for the reaction to go at atmospheric pressure, or as already indicated if its boiling point is lower, then the reaction must be conducted at supraatmospheric pressure. Within the context of this invention an inert solvent is defined as a solvent which can withstand the high reaction temperatures involved in the cyclization process without undergoing significant decomposition and which does not react with either the starting material or the product. Examples of inert solvents are aromatic solvents including hetereoaromatic and polycyclic aromatic solvents, alkylated aromatic solvents and halogenated aromatic solvents, saturated cyclic and acyclic hydrocarbons, organic esters including alkyl, phenyl and benzyl esters, and organic ethers including diphenyl ether, among others. More specific examples are methyl and t-butyl esters, decalin, 1-methylnaphthalene, naphthalene and biphenyl. Other suitable inert solvents may also be used including ketones, halogenated aliphatic hydrocarbons aliphatic esters and alcohols, among many others. Solvents which should be avoided since they are not within the above definition of an inert solvent include olefins, primary and secondary amines and carboxylic acids.

Typically, when the cyclization reaction is conducted in the liquid phase, the concentration of the alpha-vinyl cinnamic acid or ester in the solvent may be varied over a broad range. Typically, the cinnamic acid or ester is present in an amount of about 0.001 moles to 1.0 moles per liter of the solvent.

The alpha-vinyl cinnamic acid and ester thereof employed as a starting material for the cyclization process has the following chemical formula

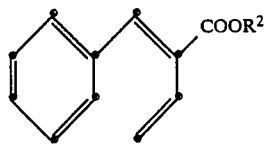

wherein $R^1$ is selected from the group consisting of neutral, electron-donating and electron-withdrawing groups and $R^2$ is selected from the group consisting of hydrogen, $(C_1-C_{12})$alkyl, $(C_6-C_{12})$aryl, $(C_6-C_{12})$alkylaryl and $(C_6-C_{12})$aralkyl.

Examples of the $R^1$ groups are halo and $(C_1-C_{12})$alkyl, acyl, acyloxy, carboxy, carbalkoxy alkylthiol or alkoxy, among others. The aromatic ring of the alpha-vinyl cinnamic acid or ester thereof may be substituted at any position, although preferred positions are the ortho and para positions of the ring with respect to the carboxy-containing residue. Examples of the substituents are carbomethoxy, methyl, isopropyl, methoxy and acetoxy, among others. However, a variety of other substituents may also be attached to the aromatic ring of the cinnamic acid or ester thereof.

If the ring substitution is in either the para or ortho position, the products are entirely predictable. More specifically, para substituted alpha-vinyl cinnamates undergo ring closure to yield 6-substituted 3,4-dihydro 2-naphthanoates and ortho-substituted alpha-vinyl cinnamates yield 8-substituted 3,4-dihydro 2-naphthanoates. By means of example, methyl p-methoxy-alpha-vinyl cinnamate undergoes ring closure to yield methyl 6-methoxy-3,4-dihydro-2-naphthanoate and methyl o-methoxy-alpha-vinyl cinnamate yield methyl 8-methoxy-3,4-dihydro 2-naphthanoate. On the other hand, the meta substitution of the aromatic ring of the cinnamic acids or esters leads to a mixture of products. For example, the ring closure of methyl m-methoxy-alpha-vinyl cinnamate yields an about 65:35 mixture of 5-methoxy and 7-methoxy substituted 3,4-dihydro-2-naphthanoate methyl esters, respectively. Clearly, the present process enables the preparation of these unique compounds, although they are not obtainable in a form which is substantially free of other isomers.

Although the $R^2$ ester function of the cinnamic acid may be derived from any alkyl or aryl group, the methyl ester is preferred due to its high volatility, particularly when the cyclization step is conducted in the vapor phase. The selection of the specific ester derivative is of lesser importance when the reaction is conducted in the liquid phase, and therefore there is more latitude in the choice of the specific ester utilized.

The alpha-vinyl cinnamic acid or ester thereof may be obtained by contacting crotonic anhydride and a benzaldehyde substituted with halo or $(C_1-C_{12})$alkyl, acyl, acyloxy, carboxy, carbalkoxy, alkylthiol or alkoxyl, among other substituents. The crotonic anhydride and the substituted benzaldehydes are commercially available or may be prepared by methods known in the art which need not be described herein.

The condensation of crotonic anhydride with an aromatic aldehyde to generate a ring-substituted alpha-vinyl cinnamic acid derivative is known (Kuhn R., and Ishikawa, S., Chem. Ber. 64: 2347 (1931); Kresze, G., and Mavromatis, A., Tet. 34: 697 (1978)) as well as the subsequent esterification of the compounds (Kresze, G. and Mavromatis, A., supra). However, the incorporation of the prior art process as a preliminary step in the synthesis of substituted naphthanoic acids is novel and unobvious.

The process of preparing a 2-naphthanoic acid or ester thereof comprises a cyclization step as described supra and a dehydrogenating step whereby the 3,4-dihydro 2-naphthanoic acid or ester thereof is converted to the corresponding 2-naphthanoic acid or ester thereof.

A substantial body of information on the dehydrogenation of partially saturated, polycyclic organic compounds has been available. Although this dehydrogenation reaction generally proceeds without difficulties, there are innumerable examples in the prior art of unexpected rearrangements which occur in the course of these reactions because they are conducted at high temperatures, i.e., 175° C. to 300° C., and in the presence of very active catalysts. However, in accordance with this invention, the dehydrogenation of the intermediate 3,4-dihydro 2-naphthanoic acids or esters thereof can be attained while preserving the specific substitution pattern of the compound.

The dehydrogenation step is typically conducted at a temperature of about 150° C. to 350° C., and more preferably about 175° C. to 250° C., and at a pressure of about 1 mmHg to 5 atmospheres, and more preferably about 10 mmHg to 1 atmospheres. The dehydrogenation of the 3,4-dihydro 2-naphthanoic acid or ester thereof may be readily performed in the presence of a standard dehydrogenation catalyst such as 5% Pd on carbon. Suitably any homogeneous or heterogeneous catalyst comprising at least one group VIII transition metal may be utilized. Examples of these metals are ruthenium, rhodium, platinum, palladium, iridium and osmium. These catalysts and dehydrogenation reactions in general are known in the art (Hansch, Chem. Rev. 53: 353 (1953); Pines and Goetschel, J. Org. Chem. 30: 3530 (1965); March, J., Advanced Org. Chem.: Reaction Mechanisms, McGraw-Hill Book Co. (1977 year); House, H. O., Modern Org. Reactions, Benjamen, W. A., Inc., Eds. (1972 year)).

The dehydrogenation reaction may be carried out in the presence of a hydrogen-acceptor such as an olefin or a carbonyl-containing compound. The number of olefins and ketones or aldehydes which are capable of accepting hydrogen atoms released during the dehydrogenation step is quite large. (Brieger, G., and Nestrick, T. J., Chem. Rev. 74: 567 (1974); Kolomnikov, I. S., Kukolev, V. P., and Vol'pin, M. E., Russ. Chem. Rev. 43: 399 (1974)). Among the carbonyl-containing compounds, the ketones are preferred. By means of example, methyl 6-methyl-3,4-dihydro-2-naphthanoate (derived from methyl alpha-vinyl cinnamate as described in Example 2 below) is readily dehydrogenated by commercially available 5% Pd on carbon in decalin at reflux to give methyl 6-methyl-2-naphthanoate with a 51% yield. By the same procedure, methyl 6-carbomethoxy-3,4-dihydro-2-naphthanoate is converted to dimethyl 2,6-naphthandioate with a 69% yield.

The synthesis of a desired substituted dihydro-2-naphthanoic acid or ester thereof from an aromatic aldehyde and crotonic anhydride is an unobvious route based on the prior art known at the time of this invention. More specifically, although ring closure was observed by the prior art for the generation of simple dihydronaphthalenes it is unobvious that such reaction would occur for alpha-vinyl cinnamic acids or esters thereof of various substitution patterns. In particular, prior to this invention it was not known and could not have been expected based on the information available at the time that the introduction of a carboxylic acid group on the diene substituent would not interfere with the cyclization reaction and that the carboxylic acid group would be retained in the molecule under the harsh conditions of the cyclization reaction of the invention.

The entire process (including the cyclization reaction and the dehydrogenation reaction) may just as easily be carried out in one vessel by including the dehydrogenation catalyst in the reaction vessel at the start of the cyclization reaction, thereby permitting the in situ dehydrogenation of the dihydronaphthalene derivative as it is produced. The conditions for this process are similar to those of the thermal ring closure or cyclization of the cinnamic acid or ester. This "one-vessel" cyclization-hydrogenation process may, for example, be performed by heating a solution of the alpha-vinyl cinnamic acid or ester thereof in a high boiling inert solvent in the presence of a dehydrogenation catalyst using an inert gas purge to remove hydgrogen gas as it is formed. The operable temperatures of this process are only limited by the operator since in principle supraatmospheric pressures may be used, i.e., an autoclave, with or without a gas purge. This allows the operator of the process to attain any desired temperature while still maintaining the solvent in the liquid phase. Typically, the temperatures used in this process are about 150° C. to 400° C. However, higher temperatures may be utilized, such as up to and in excess of about 750° C.

Although the examples provided with this application all use palladium on carbon as the dehydrogenation catalyst, similar results are obtained for other catalysts such as those described above.

The dehydrogenation reaction may be carried out in the absence of a gas purge or hydrogen-acceptor if a loss in reaction rate and yield is acceptable.

The "one vessel" process may also be operated in the vapor phase under the conditions described supra.

Having now generally described this invention, the same will be better understood by reference to certain specific examples, which are included herein for purposes of illustration only and are not intended to be limiting of the invention or any embodiment thereof, unless so specified.

EXAMPLES

Example 1

This example is a general procedure for the vapor phase cyclization of the alpha-vinyl cinnamate esters to the desired 3,4-dihydro-2-naphthanoates. All the alpha-vinyl cinnamate esters in this and subsequent examples were synthesized using procedures described by Kuhn, R., and Ishikawa, S., supra, and Kresze, G., and Mavromatis, supra.

A quartz tube measuring 14 inches in length (including a pair of 24/40 ground glass joints at each end), 1 inch in diameter, and possessing indentations at 3 inches from the base is used as a reactor. A quartz wool plug is placed in the reactor in contact with the indentations and the top of the reactor is fitted with a four-necked reactor head which is capable of holding a quartz thermal-couple well, an inert gas flow inlet, a septum capped hole (to be used as an inlet for the starting material), and a hole which is large enough to pass in a supply of fine chips (Vycor®) and which can readily be sealed after filling the reactor. This last requirement is best met using a fitted ground glass joint and seal.

After assembly of the head, reactor and thermal well, the reactor is filled with the fine chips (Vycor®) to a height of 20 cm, sealed and placed in a 12-inch electric furnace so that the entire packed portion of the reactor is centered in the furnace. A flask equipped with a side arm (to be used as a gas outlet) is connected to the bottom of the reactor. An inert gas purge, in this case argon, is established at a level of 100 mL/min. The reactor is then heated to 400°–425° C. and maintained at that level for the duration of the reaction.

Using a syringe drive to regulate the rate of addition, 2.12 grams (11.3 mmol) of liquid methyl alpha-vinyl cinnamate are added to the reactor via syringe at a rate of 1 mL/min using the septum capped inlet. The product is collected in the bottom flask and weighs 1.94 grams (10.3 mmol). This represents a 92% yield and gas chromatographic analysis reveals the material to be pure. The compound is known and is identified on the basis of its nuclear magnetic resonance spectrum.

400 MHz NMR(CDCl$_3$): 2.61 (t, 3H), 2.86 (t, 3H), 3.82 (s, 3H), 7.14–7.26 (m, 5H), 7.53 (s, 1H).

Examples 2 through 5 herebelow demonstrate the general utility of the vapor phase version of this process.

Example 2

Following the procedure in Example 1, 5.30 grams (26.2 mmol) of liquid methyl p-methyl-alpha-vinyl cinnamate is converted to 4.90 grams (24.3 mmol) of pure (97%) methyl 6-methyl-3,4-dihydro-2-naphthanoate. This represents a 92% yield. The compound is characterized on the basis of its spectral characteristics and elemental analysis.

400 MHz NMR(CDCl$_3$): 2.35 (s, 3H), 2.59 (t, 2H), 2.83 (t, 2H), 3.71 (s, 3H), 6.99 (s, 1H), 7.01 (d, 2H, J=9 Hz), 7.09 (d, 2H, J=9 Hz), 7.50 (s, 1H).

IR(KBr): 1708, 1278 cm(−1).

Mass spectrum: (M+/e) 115, 128, 143, 202.

Elemental Analysis: Calculated: C, 77.20; H, 6.98. Found: C, 76.95; H, 6.93.

MP: 50°–51° C.

Example 3

Following the procedure in Example 1, 1.119 grams (5.01 mmol) of liquid methyl p-chloro-alpha-vinyl cinnamate are converted to 0.896 grams (4.01 mmol) of methyl 6-chloro-3,4-dihydro-2-naphthanoate. This represents a yield of 80%. The compound was characterized based on its spectral characteristics and its elemental analysis.

400 MHz NMR(CDCl$_3$): 2.60 (t, 2H), 2.85 (t, 2H), 3.72 (S, 3H), 7.11 (d, 1H, J=9 Hz), 7.17 (d, 1H, J=9 Hz), 7.16 (S, 1H), 7.48 (S, 1H).

IR(CH$_2$Cl$_2$): 1713, 1270 cm(−1).

MS: (M+/e): 222.

Elemental Analysis: Calculated: C, 64.73; H, 4.98; Cl, 15.92. Found: C, 64.84; H, 4.93; Cl, 15.93.

MP: 65°–67° C.

Example 4

Following the procedure in Example 1, 1.96 grams (8.99 mmol) of liquid methyl p-methoxy-a-vinyl cinnamate are converted to 1.20 grams (5.56 mmol) of methyl 6-methoxy-3,4-dihydro-2-naphthanoate. This represents a 61% yield. The compound is known (Hansch, supra) and is characterized based on a comparison of its NMR spectrum and melting point with the literature.

400 MHz NMR(CDCl$_3$): 2.60 (t, 2H), 2.85 (t, 2H), 3.80 (s, 3H), 3.82 (s, 3H), 6.72 (s, 1H), 6.73 (d, 1H, J=9 Hz), 7.13 (d, 1H, J=9 Hz), 7.49 (s, 1H).

MP: 46°–47° C. (lit. 50°–51° C.).

Example 5

Following the procedure in Example 1, 0.770 grams (3.16 mmol) of methyl p-carbomethoxy-alpha-vinyl cinnamate (as a solution in 1.5 grams of methyl acetate) are converted to 0.440 grams (1,80 mmol) of methyl 6-carbomethoxy-3,4-dihydro-2-naphthanoate. This represents a 56% yield. The compound is known (Pines and Goetschel, supra) and is based on a comparison of its NMR spectrum and melting point.

400 MHz NMR(CDCl$_3$): 2.65 (t, 2H), 2.92 (t, 2H), 3.84 (s, 3H), 3.92 (s, 3H), 7.23 (d, 1H, J=9 Hz), 7.53 (s, 1H), 7.85 (s, 1H), 7.87 (d, 1H, J=9 Hz).

MP: 121°–123° C. (lit. 126° C.).

Example 6

This example demonstrates the feasibility of using ortho substituted alpha-vinyl cinnamate esters to generate 8-substituted 3,4-dihydro-2-naphthanoate esters.

Following the procedure in Example 1, 1.99 grams (9.21 mmol) of methyl o-methoxy-alpha-vinyl cinnamate (added as a solution in 3.06 of mehylacetate) is converted to 1.84 grams (8.52 mmol) of mehyl 8-methoxy-3,4-dihydro-2-naphthanoate. This represents a 92% yield. The liquid product is identified on the basis of its spectral properties and elemental analysis.

400 MHz NMR(CDCl$_3$): 2.57 (t, 2H), 2.82 (t, 2H), 3.81 (s, 3H), 3.85 (s, 3H), 6.73 (d, 1H, J=9 Hz), 6.77 (d, 1H, J=9 Hz) 7.20 (t, 1H, J=9 Hz), 7.95 (s, 1H).

IR(CH$_2$Cl$_2$): 1707 cm$^{-1}$.

MS(M+/e): 218.

Elemental Analysis: Calculated: C, 71.54; H, 6.47. Found: C, 71.88; H, 6.42.

Example 7

This example demonstrates the limitation imposed in the case of meta substituted alpha-vinyl cinnamate esters where the compound cyclizes readily but is unselective, giving 2 separable isomers.

Following the procedure in Example 1, 0.950 grams (4.40 mmol) of methyl m-methoxy-alpha-vinyl cinnamate is cyclized to a mixture of two distinguishable methoxy substituted 3,4-dihydro-2-naphthanoate esters which are separated by liquid chromatography to give 0.580 grams (2.69 mmol) of methyl 5-methoxy-3,4-dihydro-2-naphthanoate and 0.340 grams (1.58 mmol) of methyl 7-methoxy-3,4-dihydro-2-naphthanoate. This represents a 61% and a 36% yield, respectively. The compounds are identified on the basis of their spectral properties and elemental analysis. These are listed below.

METHYL 5-METHOXY-3,4-DIHYDRO-2-NAPHTHANOATE

400 MHz MNR(CDCl$_3$): 2.59 (t, 2H), 2.87 (t, 2H), 3.81 (s, 3H), 3.84 (s, 3H), 6.84 (d, 1H, J=9 Hz), 6.85 (d, 1H, J=9 Hz), 7.17 (t, 1H, J=9 Hz), 7.49 (s, 1H).

IR(CH$_2$Cl$_2$): 1707 cm$^{-1}$.

MS: (M+/e) 218.

Elemental analysis Calculated: C, 71.54; H, 6.47. Found: C, 71.71; H, 6.47.

MP: 54°–56° C.

METHYL 7-METHYL-3,4-DIHYDRO-2-NAPHTHANOATE

400 MHz NMR(CDCl$_3$): 2.59 (t, 2H), 2.80 (t, 2H), 3.80 (s, 3H), 3.82 (s, 3H), 6.77 (d, 1H, J=1 Hz) 6.80 (dd, 1H, J=1,9 Hz), 7.07 (d, 1H, J=9 Hz), 7.49 (s, 1H).

Example 8

This example demonstrates the feasibility of operating this process in the liquid phase. Using a 100-mL round-bottom flask as a reaction vessel, a solution of 0.530 grams (2.62 mmol) of methyl p-methyl alpha-vinyl cinnamate in 53 mL of decalin is heated at reflux for 40 hours. Most of the decalin is removed by distillation and the residue separated by chromatography using 3% ethyl acetate in hexane as eluent. This procedure yields 0.130 grams (0.64 mmol) of pure methyl 6-methyl-3,4-dihydro-2-naphthanoate. This corresponds to a yield of 24%. The product is identical to that obtained in the vapor phase reaction described in Example 2.

The following examples demonstrate the utility of a "one vessel" process which includes a dehydrogenation catalyst in the reaction vessel so that the useful 2-naphthanoic acid or ester is generated directly. The products in this section are all known in the literature and are identified on the basis of their characteristic NMR spectra.

Example 9

Using a 100-mL round-bottomed flask as a reaction vessel, a solution of 0.533 grams of methyl p-methyl alpha-vinyl cinnamate in 53 mL of decalin containing 0.103 grams of 5% Pd on carbon is heated at reflux for 40 hours under a slow, continuous stream of an inert gas (argon). The product is isolated by adding the solution to a chromatography column and eluting with 3% ethyl acetate in hexane. The yield is 0.257 grams (49%) of pure methyl 6-methyl-2-naphthanoate.

Example 10

Using a 100-mL round-bottomed flask as a reaction vessel, a solution of 0.855 grams of methyl p-carbomethoxy-alpha-vinyl cinnamate in 70 mL of 1-methylnaphthalene containing 0.250 grams of 5% Pd on carbon is heated at reflux for 5 hours using a slow, continuous purge of argon. The mixture is then allowed to cool slightly, is filtered to remove the catalyst, and the solvent is removed under vacuum using distillation. The residue is redissolved in 10 mL of ethyl acetate. The ethyl acetate initially dissolves all the residue and then crystals begin to form giving 0.365 grams of pure dimethyl 2,6-naphthalene dicarboxylate. Chromatography yields another 0.105 grams of the desired product for a combined yield of 0.470 grams (55%) of pure dimethyl 2,6-naphthalene dicarboxylic acid.

Example 11

Using a 100-mL round-bottomed flask as a reaction vessel, a solution of 0.512 grams of p-methoxy-alpha-vinyl cinnamic acid in 50 mL of 1-methylnaphthalene containing 0.100 grams of 5% Pd on carbon is heated at reflux for 5 hours using a slow, continuous purge of argon. The product is isolated by adding the product solution to a chromatography column and eluting first with pure hexane until no remaining 1-methylnaphthalene can be detected by thin layer chromatography and following this elution with a solvent mixture of 1% acetic acid/9% ethyl acetate/hexane. The yield of purified 6-methoxy-2-naphthanoic acid is 0.267 grams (53%).

Example 12

Following the procedure in Example 11, 0.500 grams of o-methoxy-alpha-vinyl cinnamic acid are converted to 0.295 grams (60%) of purified 8-methoxy-2-nephthanoic acid.

Example 13

Following the procedure in Example 11, 0.507 grams of p-methyl alpha-vinyl cinnamic acid are converted to 0.234 grams (47%) of purified 6-methyl-2-naphthanoic acid.

Example 14

Following the procedure in Example 11, 0.503 grams of alpha-vinyl cinnamic acid are converted to 0.222 grams (45%) of purified 2-naphthanoic acid.

The invention now being fully described, it will be apparent to one of ordinary skill in the art that many changes and modifications can be made thereto without departing from the spirit or scope of the invention as set forth herein.

What is claimed is:

1. A process for preparing a 3,4-dihydro 2-naphthanoic acid or an ester thereof, comprising
   heating an alpha-vinyl cinnamic acid or a ($C_1$–$C_{12}$)alkyl, ($C_6$–$C_{12}$)aryl, ($C_6$–$C_{12}$)alkylaryl or ($C_6$–$C_{12}$)aralkyl ester thereof at a temperature effective to cyclize said acid or ester thereof and obtain the corresponding 3,4-dihydro 2-naphthanoic acid or ester thereof.

2. The process of claim 1, wherein the heating is conducted in the vapor phase at a temperature of about 200° C. to 800° C. and a pressure of about 0.1 mmHg to 5 atm.

3. The process of claim 2, wherein the heating is conducted at a temperature of about 350° C. to 550° C. and a pressure of about 10 mmHg to 1,500 mmHg.

4. The process of claim 1, wherein the heating is conducted in an inert solvent at a temperature of about 150° C. to 500° C.

5. The process of claim 4, wherein the heating is conducted at a temperature of about 180° C. to 400° C.

6. The process of claim 4, wherein the inert solvent has a boiling point greater than the reaction temperature.

7. The process of claim 1, wherein the alpha-vinyl cinnamic acid or ester thereof is substituted with halo or ($C_1$–$C_{12}$)alkyl, acyloxy, carboxy, carbalkoxy, acyl, alkylthio or alkoxy.

8. The process of claim 7, wherein the acid is substituted at the ortho or para positions.

* * * * *